(12) United States Patent
Chu

(10) Patent No.: US 9,795,401 B2
(45) Date of Patent: Oct. 24, 2017

(54) MEDICAL RETRIEVAL DEVICES AND RELATED METHODS OF USE

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 332 days.

(21) Appl. No.: 14/555,070

(22) Filed: Nov. 26, 2014

(65) Prior Publication Data

US 2015/0148814 A1   May 28, 2015

Related U.S. Application Data

(60) Provisional application No. 61/909,515, filed on Nov. 27, 2013.

(51) Int. Cl.
*A61B 17/22* (2006.01)
*A61B 17/221* (2006.01)

(52) U.S. Cl.
CPC .... *A61B 17/221* (2013.01); *A61B 2017/2215* (2013.01)

(58) Field of Classification Search
CPC .................. A61B 17/221; A61B 2017/2215
See application file for complete search history.

(56) References Cited

U.S. PATENT DOCUMENTS

| | | | |
|---|---|---|---|
| 5,906,622 A * | 5/1999 | Lippitt | A61B 17/221 606/113 |
| 5,924,175 A | 7/1999 | Lippitt et al. | |
| 6,458,145 B1 | 10/2002 | Ravenscroft et al. | |
| 6,626,915 B2 | 9/2003 | Leveillee | |
| 7,041,108 B2 | 5/2006 | Lippitt et al. | |
| 7,210,210 B2 | 5/2007 | Lippitt et al. | |
| 2002/0068944 A1 * | 6/2002 | White | A61B 17/22031 606/114 |

* cited by examiner

*Primary Examiner* — Richard Louis
(74) *Attorney, Agent, or Firm* — Bookoff McAndrews, PLLC

(57) ABSTRACT

A medical device that may include a plurality of first branch members, and a plurality of second branch members is disclosed. The medical device may also include a first movable member, and a second movable member. The plurality of first and second branch members and the first and second movable members may form a basket movable between a collapsed configuration and an expanded configuration.

9 Claims, 9 Drawing Sheets

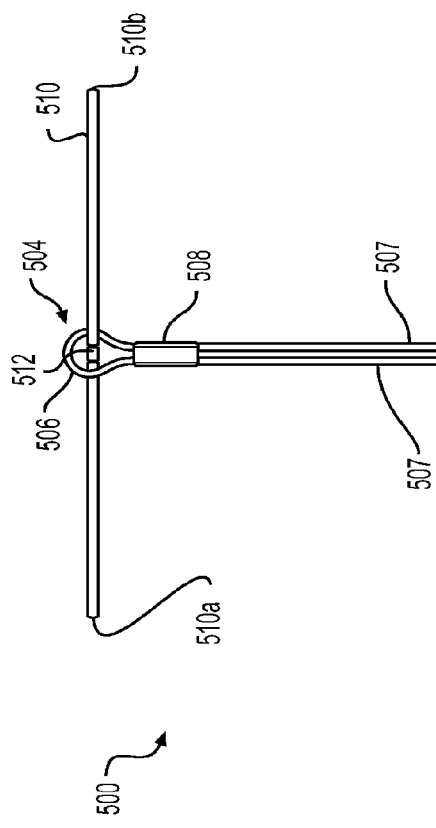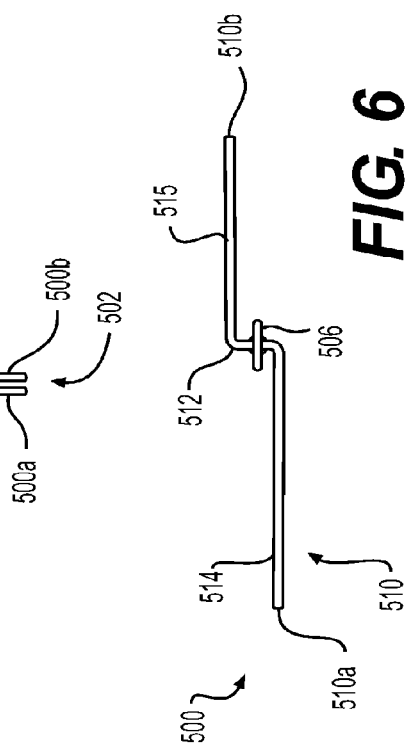

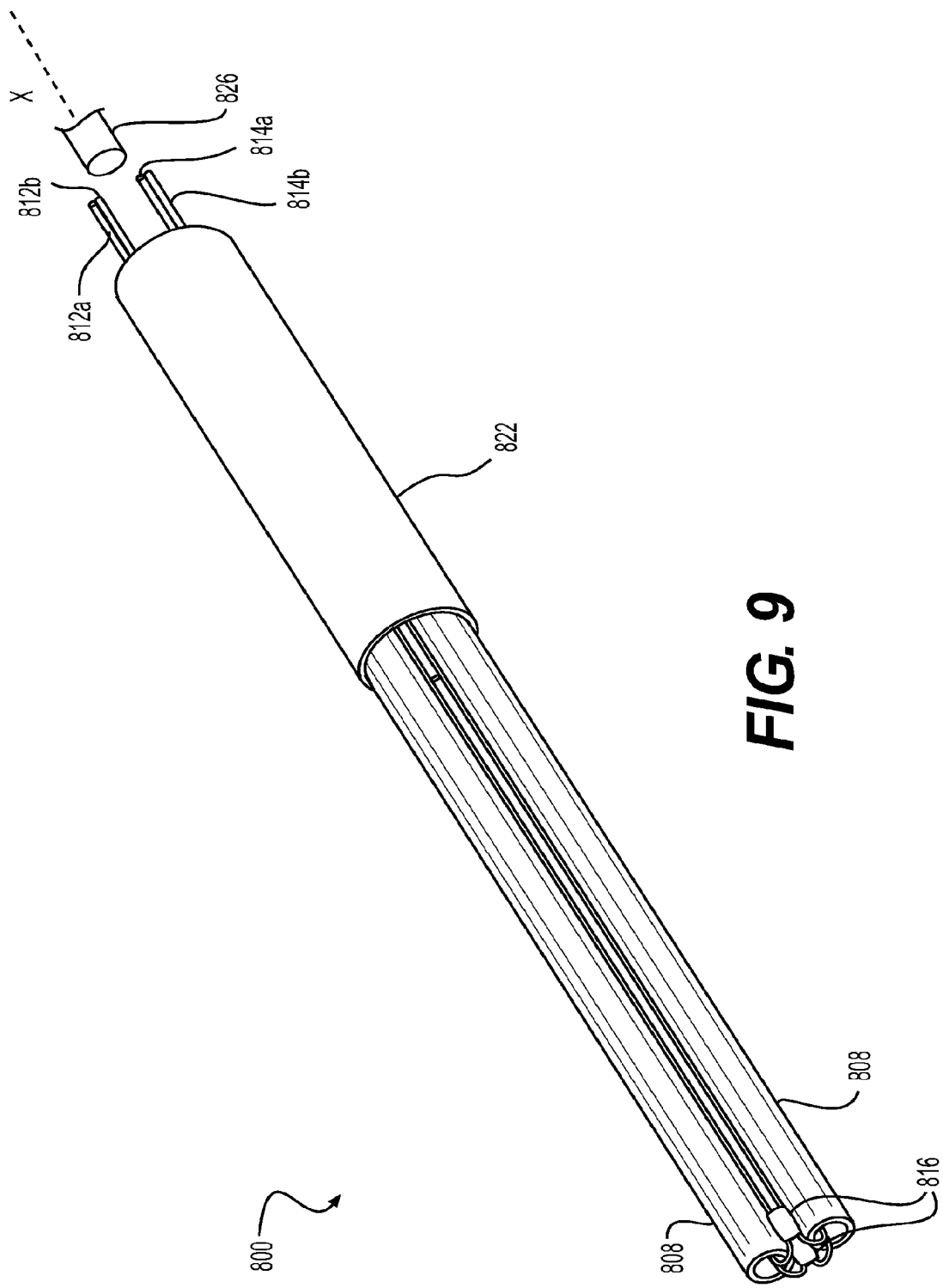

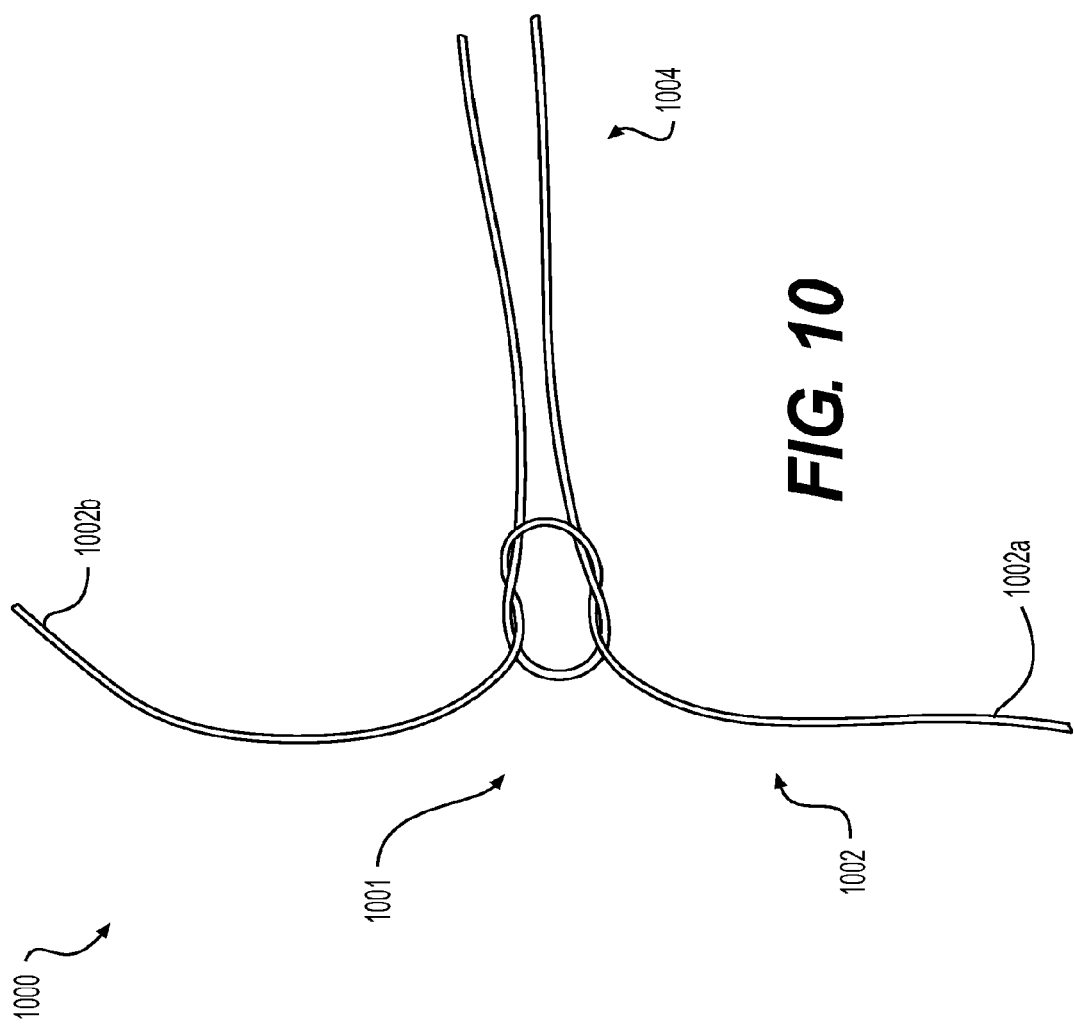

MEDICAL RETRIEVAL DEVICES AND RELATED METHODS OF USE

CROSS-REFERENCE TO RELATED APPLICATION

This patent application claims benefit of priority under 35 U.S.C. §119 to U.S. Provisional Patent Application No. 61/909,515, filed Nov. 27, 2013, the entirety of which is incorporated herein by reference.

TECHNICAL FIELD

Various embodiments of the present disclosure relate generally to medical retrieval devices and related systems and methods. More specifically, the present disclosure relates to devices, systems, and methods for retrieving objects within a patient.

BACKGROUND

Medical retrieval devices are often utilized for removing organic material (e.g., blood clots, tissue, and biological concretions such as urinary, biliary, and pancreatic stones) and inorganic material (e.g., components of a medical device or other foreign matter), which may obstruct or otherwise be present within a patient's body cavities. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy (PNCL) procedure. Further, lithotripsy and ureteroscopy, for example, are used to treat urinary calculi (e.g., kidney stones) in the ureter of a patient.

Further, known medical retrieval devices are complex, requiring many components and labor-intensive manufacturing processes. The assembly of small parts often requires visual magnification and specialized training. The available joining mechanisms often increase the profile of the medical retrieval devices beyond optimal design parameters, and are often the weakest structural points. These drawbacks result in medical retrieval devices that are bulky, expensive, and prone to failure.

Thus, there remains a need for improved medical retrieval devices having reduced profiles and fewer components.

SUMMARY OF THE DISCLOSURE

The present disclosure includes medical retrieval devices and related methods of use.

In accordance with an embodiment of the disclosure, a medical device may include a plurality of first branch members, and a plurality of second branch. The medical device may also include a first movable member, and a second movable member. The plurality of first and second branch members and the first and second movable members may form a basket movable between a collapsed configuration and an expanded configuration.

Various embodiments of the disclosure may include one or more of the following aspects: wherein a middle portion of the first movable member is fixed with respect to at least one of the plurality of second branch members, and a middle portion of the second movable member is fixed with respect to at least one of the plurality of second branch members; wherein the first and second branch members alternate circumferentially about a longitudinal axis of the medical device; wherein two portions of the first movable member extend distally from different second branch members and back through a same first branch member; wherein two ends of the second movable member extends distally from different second branch members and back through a same first branch member; wherein the respective two ends of each of the first and second movable members extend through different first branch members; wherein each of the plurality of first branch members includes a tube having a portion of at least one of the first and second movable members disposed therethrough; wherein each of the plurality of second branch members includes a tube having a portion of each of the first and second movable members disposed therethrough; wherein each second branch member is formed from portions of the first and second movable members joined at a distal end of the medical device; further including a sheath coupled to a proximal end of each of the plurality of first and second branch members, wherein at least one end of each of the plurality of first and second movable members extend proximally within the sheath; wherein a midpoint of the first movable member is fixed to one of the plurality of second branch members; wherein a midpoint of the second movable member is fixed to another of the plurality of second branch members; wherein each of the plurality of second branch members includes an eyelet disposed at a distal end of the second branch member; wherein the first movable member extends through an eyelet of one of the plurality of second branch members, and the second movable member extends through an eyelet of another of the plurality of second branch members; wherein the first and second movable members each include a first end, a second end, and a lock section disposed between the first and second ends, the lock section being coupled to each of the first and second ends by a bend that is offset from the lengths of the first and second ends, and the lock section is secured to the eyelet; wherein the plurality of second branch members are joined at a proximal end to form a v-shape; wherein each of the plurality of second branch members include a transverse bore at a distal end, the first movable member is disposed through the transverse bore of one of the second branch members, and the second movable member is disposed through the transverse bore of another of the second branch members; wherein the plurality of second branch members, the first movable member, and the second movable member are joined in a branch assembly.

In accordance with an embodiment of the disclosure, a medical device may include a pair of first branch members, and a pair of second branch members. The medical device may also include a first movable member, and a second movable member. The first and second movable members may each have a portion fixed with respect to both of the second branch members.

In accordance with an embodiment of the disclosure, a medical device may include a plurality of first branch members, and a plurality of second branch members. The medical device may also include a first movable member, and a second movable member. Opposing ends of the first movable member may extend from one of the plurality of second branch members though each of the plurality of first branch members, and opposing ends of the second movable member may extend from another of the plurality of second branch members through each of the plurality of first branch members.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

FIG. 5 is a partial front view illustration of a branch member and movable member in accordance with an embodiment of the present disclosure.

FIG. 6 is a top view illustration of the branch member and movable member in accordance with an embodiment of the present disclosure.

FIG. 9 is a partial side perspective view illustration of the medical retrieval device of FIG. 8 in a collapsed configuration.

FIG. 10 is a front view illustration of a fastening mechanism in accordance with an embodiment of the present disclosure.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts.

Figure 1:
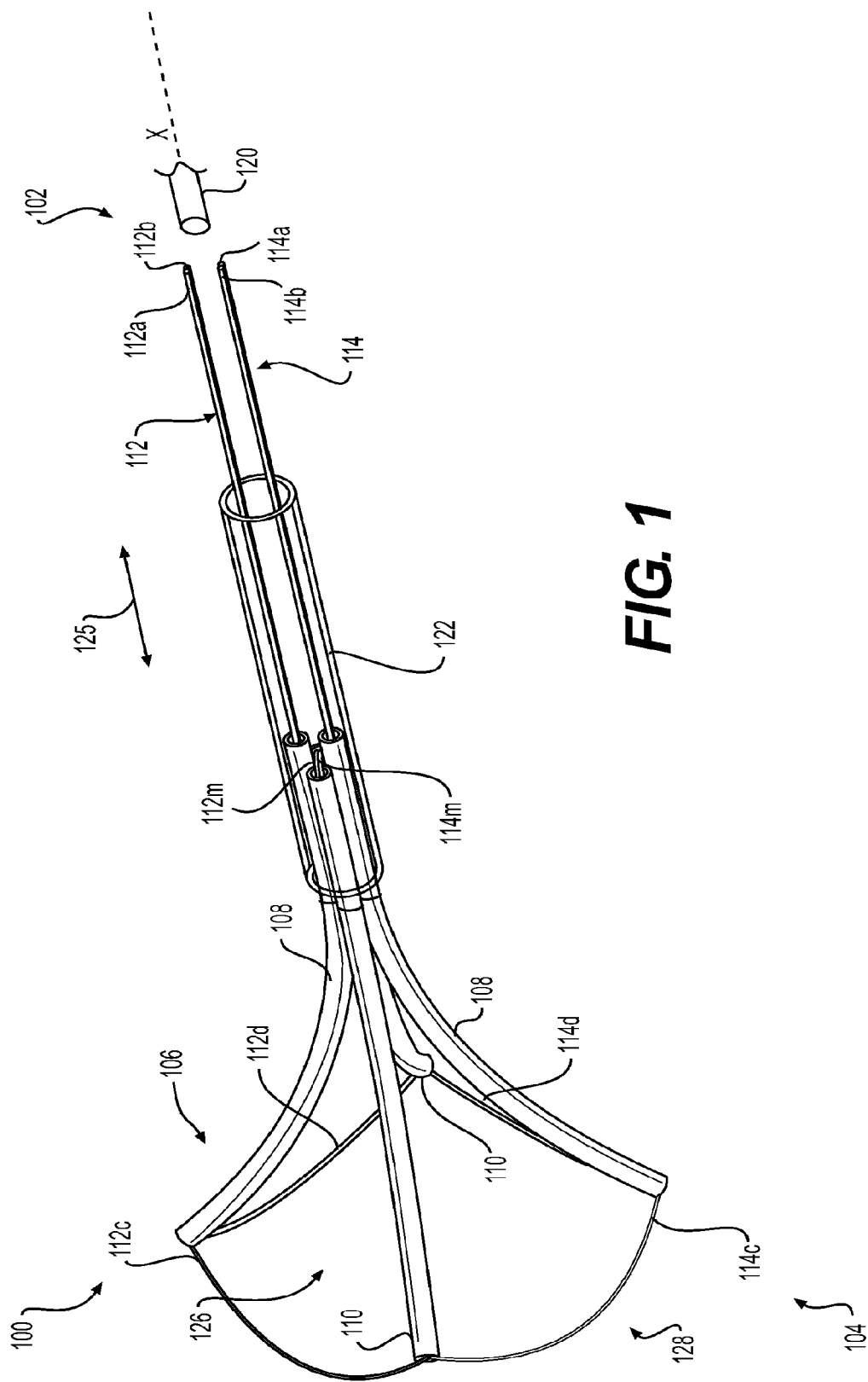
FIG. 1 is a partial side perspective view illustration of a medical retrieval device in an expanded configuration in accordance with an embodiment of the present disclosure.

As shown in FIG. 1, a medical device 100 according to an exemplary embodiment of the present disclosure may extend from a proximal end 102 toward a distal end 104. Medical device 100 may include a basket 106 disposed at distal end 104, and may be configured to reciprocally move between a collapsed configuration and an expanded configuration. In the embodiment shown in FIG. 1, basket 106 is in the expanded configuration. In the expanded configuration, a plurality of first branch members 108 and a plurality of second branch members 110 may be disposed radially outward about a longitudinal axis X of medical device 100. The plurality of first and second branch members 108, 110 may be circumferentially spaced apart from one another about longitudinal axis X. First branch members 108 may alternate with second branch members 110 such that each first branch member 108 may be circumferentially adjacent at least two second branch members 110. Similarly, each second branch member 110 may be circumferentially adjacent to at least two first branch members 108. In the embodiment shown in FIG. 1, two first branch members 108 and two second branch members 110 are disposed circumferentially about longitudinal axis X, and each first branch member 108 may be disposed approximately 90° from an adjacent second branch member 110. However, it should be noted that any other suitable number of first and second branch members 108, 110 may alternatively be utilized, if desired.

In some embodiments, first and second branch members 108, 110, may be substantially similar, and be formed in a tubular shape. First and second branch members 108, 110 may be formed of a polymer, such as, e.g., polyethylene terephthalate (PET), among others. First and second branch members 108, 110 may have a circumferential wall thickness of about 0.0004", and an internal diameter (ID) of about 0.006", though any other suitable wall thickness and internal diameter may alternatively be utilized.

In the embodiment of FIG. 1, medical device 100 may include a first movable member 112 having a first end 112a, a second end 112b, and a midpoint 112m. Medical device 100 may also include a second movable member 114 having a first end 114a, a second end 114b, and a midpoint 114m. First and second movable members 112, 114 may be formed of any suitable material including, but not limited to, metals, polymers, or a combination of materials. In one embodiment, first and second movable members 112, 114 may each include a metal wire coated with a polymer. In an alternative embodiment, first and second movable members 112, 114 may be each formed from two or more metals that are coaxial, for example, by being co-drawn together. First and second movable members 112, 114 may have any suitable cross-sectional profile such as, e.g., circular, rectangular, ovular, or polygonal. First and second movable members 112, 114 may be hollow. In some embodiments, portions of first and second movable members 112, 114 may be flattened, machined, extruded, drawn, or etched into a different profile than a remaining portion of first and second movable members 112, 114. In some embodiments, first and second movable members 112, 114 may be slotted to allow deflection or directional bending. In one embodiment, first and second movable members 114 may be formed with a super elastic and/or shape memory material, such as, e.g., Nitinol wires having a diameter of about 0.003". The exterior surfaces of first and second branch members 108, 110, and first and second movable members 112, 114 may be roughened, notched, slotted, etched, sand-blasted, coated or otherwise modified to provide a better gripping surface.

Midpoint 112m of first movable member 112 may be disposed proximally of the proximal ends of second branch members 110. From midpoint 112m, first movable member 112 may extend through the plurality of second branch members 110, and include bridge portions 112c and 112d that extend distally from the distal ends of separate second branch members 110 into a single first branch member 108. Midpoint 114m of second movable member 114 may be disposed proximally of the proximal ends of second branch members 110. From midpoint 114m, second movable member 114 may extend through the plurality of second branch members 110, and include bridge portions 114c and 114d that extend distally from the distal ends of separate second branch members 110 into a single first branch member 108. As shown in FIG. 1, bridge portions 112c and 112d may extend through a different first branch member 108 than bridge portions 114c and 114d extend through.

Ends 112a and 112b of first movable member 112 may extend through a respective first branch member 108 toward proximal end 102. Similarly, ends 114a and 114b of second movable member 114 may extend through a different respective first branch member 108 toward proximal end 102. First and second movable members 112 and 114 may be coupled to an actuation member 120 via ends 112a, 112b, 114a, and 114b. Actuation member 120 may be a filament, braided wire, rope, rod, or other suitable actuation member that may be coupled to an actuator (not shown). In an alternative embodiment, first and second movable members 112, 114 may be coupled to the actuator directly. The actuator may be disposed within a housing, e.g., a handle, and may encompass any suitable actuator configured to reciprocally move actuation member 120 and/or first and second movable members 112, 114 in a longitudinal direction including, but not limited to, sliding mechanisms, rotating mechanisms, pushing mechanisms, or the like.

A sheath 122 may be disposed around the proximal ends of first and second branch members 108, 110. In some embodiments, the proximal ends of first branch members 108 may be staggered from the proximal ends of second branch members 110 to facilitate attachment of first and second branch members 108, 110 within sheath 122. First and second branch members 108, 110 may be secured within sheath 122 by an adhesive, such as, e.g., glue or cyanoacrylate, or, e.g., by melting a portion of first branch member 108, second branch member 110, or an additional piece of material such as that used in branch members 108 or 110 within sheath 122. It should be noted, however, that any other suitable adhesive, or securing mechanism may alternatively be utilized. Sheath 122 may be formed of a polymer, such as, e.g., PET, among others. Adhesive may be applied around the proximal ends of first and second branch members 108, 110 to secure them within sheath 122. In some embodiments, adhesive may be applied to at least a middle portion of movable members 112, 114, such as, e.g., at approximately midpoints 112m, 114m to secure at least a middle portion of first and second movable members 112, 114 within sheath 122.

In some embodiments, middle portions of first and second movable members 112, 114 extending through second branch members 110 may be fixed with respect to second branch members 110. That is, during the reciprocal movement of basket 106 between the expanded configuration of FIG. 1, and the collapsed configuration shown only in FIG. 2, the middle portions of first and second movable members extending through second branch members 110 may move in the same manner (i.e., coextensively) with second branch members 110. It should be noted that, in some embodiments, adhesive may be omitted at the portions of first and second movable members 112, 114 that extend through respective first branch members 108 to allow displacement of first and second movable members within first branch members 108.

First and second movable members 112, 114 may move along a path 125 that travels substantially along longitudinal axis X in order to reciprocally move basket 106 between the expanded and the collapsed configurations. Thus, first and second movable members 112, 114 may slide within first branch members 108. The proximal movement of first and second movable members 112, 114 may move basket 106 from the expanded configuration of FIG. 1 to the collapsed configuration of FIG. 2. The distal movement of first and second movable members 112, 114, may move basket 106 from the collapsed configuration of FIG. 2 to the expanded configuration of FIG. 1.

In the expanded configuration, a user may manipulate medical device 100 to capture materials within a patient, such as, e.g., a kidney stone or the like. Materials may enter basket 106 via one of a plurality of side openings 126 defined by adjacent first and second branch members 108, 110, or via a distal opening 128 defined by bridge portions 112c, 112d, 114c, and 114d.

In some embodiments, first and second branch members 108, 110 may be biased (e.g., pre-bent or curved) such that in the expanded configuration of FIG. 1, the plurality of first and second branch members 108, 110 are naturally urged radially outward from longitudinal axis X. Alternatively, first and second branch members 108, 110 may be unbiased. Branch members 108, 110 may further include reinforcement, such as, e.g., a knitted filament braid with the wall of branch members 108, 110, wherein such reinforcement of the branch members further allows for deformation of the branch member in a pre-bent bias. The knitted filament may include metal, polymers, and combinations thereof.

Figure 2:
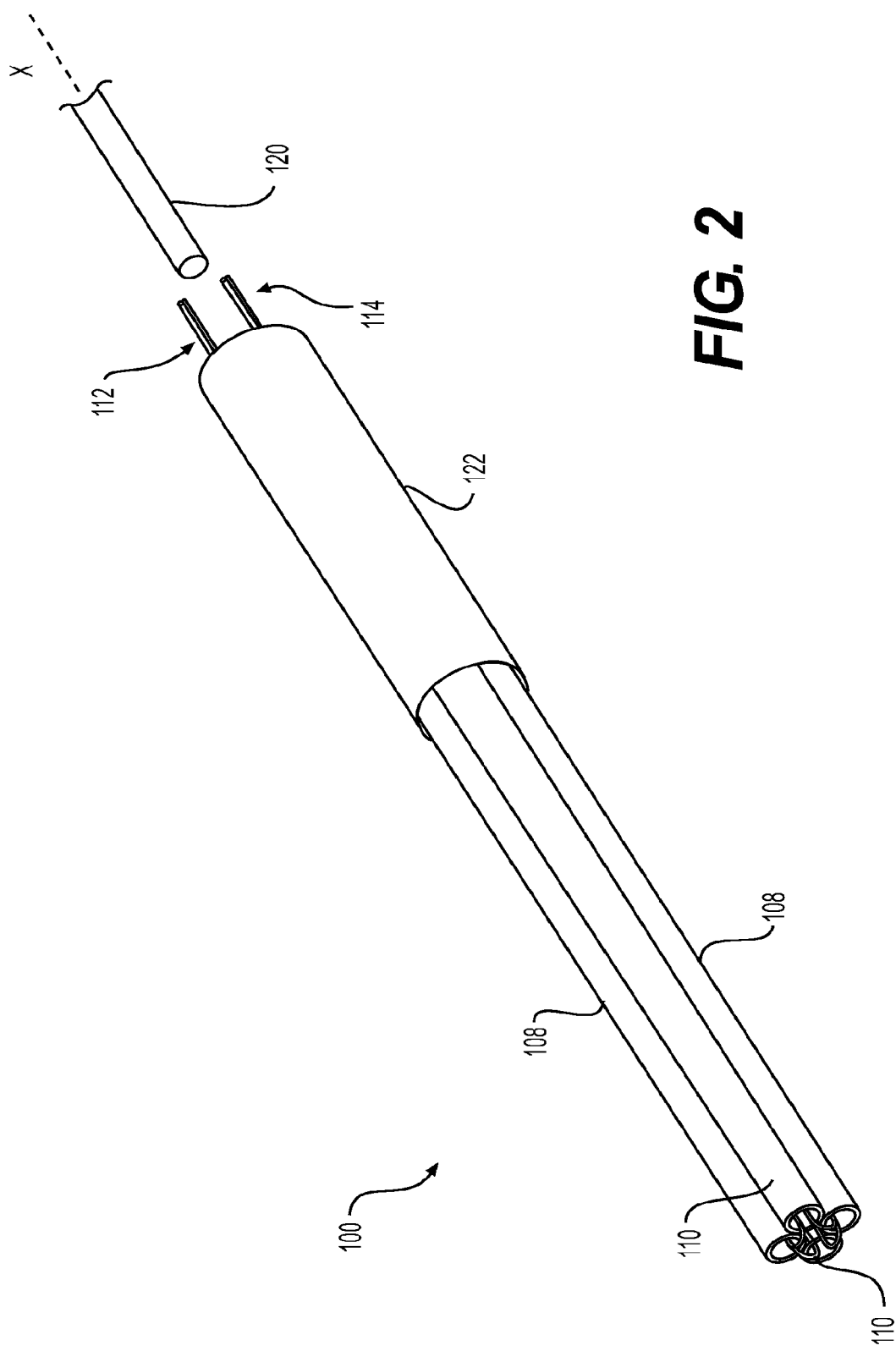
FIG. 2 is a partial side perspective view illustration of the medical retrieval device of FIG. 1 in a collapsed configuration.

In FIG. 2, medical device 100 is shown in the collapsed configuration. In the collapsed configuration, each first and second branch member 108, 110 may be substantially parallel to longitudinal axis X. That is, each first and second branch member 108, 110 may be directed radially inward toward longitudinal axis X from the expanded configuration as a result of the proximal retraction of actuation member 120 and/or first and second movable members 112, 114. In the collapsed configuration, bridge portions 112c, 112d, 114c, and 114d extending outside the distal ends of first and second branch members 108, 110 may be shorter than in the expanded configuration of medical device 100. Additionally, side openings 126 and distal opening 128 (referring to FIG. 1) may be closed in the collapsed configuration.

In an alternative embodiment, second branch members 110 may be formed from a heat shrink material, and secured around first and second movable members 112, 114. The heat shrink may extend along substantially the same portions of first and second movable members 112, 114 as second branch members 110, or any other suitable length. The heat shrink tube may be formed of a polymer, such as, e.g., PET. Before a heat shrinking process, the internal diameter of the heat shrink may be about 0.006" with a wall thickness of about 0.0004". When heat is applied to the heat shrink tube, the heat shrink tube may shrink to a smaller diameter, securing the heat shrink around the first and second movable members 112, 114 to a relatively small profile. In an alternative embodiment, one single piece of heat shrink may be used instead of a plurality of pieces. The one single piece of heat shrink may additionally surround midpoints 112m, 114m of first and second movable members 112, 114, thus forming two branches and a central bend.

In yet another alternative embodiment, four movable members may be utilized. A first pair of movable members may be secured to each other proximally within sheath 122. The first pair of movable wires may thus form a second branch member 110, and the distal end of each wire of the first pair may be directed through a respective first branch member 108 toward proximal end 102. A second pair of movable members may also be secured to each other proximally within sheath 122. The second pair of movable wires may thus form another second branch member 110, and the distal end of each wire of the second pair may be directed through a respective first branch member 108 toward proximal end 102. Alternatively, two wires may be folded to each have a 180° bend within sheath 122. Each of the folded wires may be secured at the 180° bend via, e.g., a heat shrink. Each folded wire may act as a substitute for a second branch member 110. At a distal end of medical device 100, one end of a folded wire may be threaded through a first branch member 108 toward proximal end 102, while a second end of the folded wire may be threaded through another first branch member 108 toward proximal end 102. Thus, each first branch member 108 may have two portions of two folded wires disposed therethrough.

Figure 3:
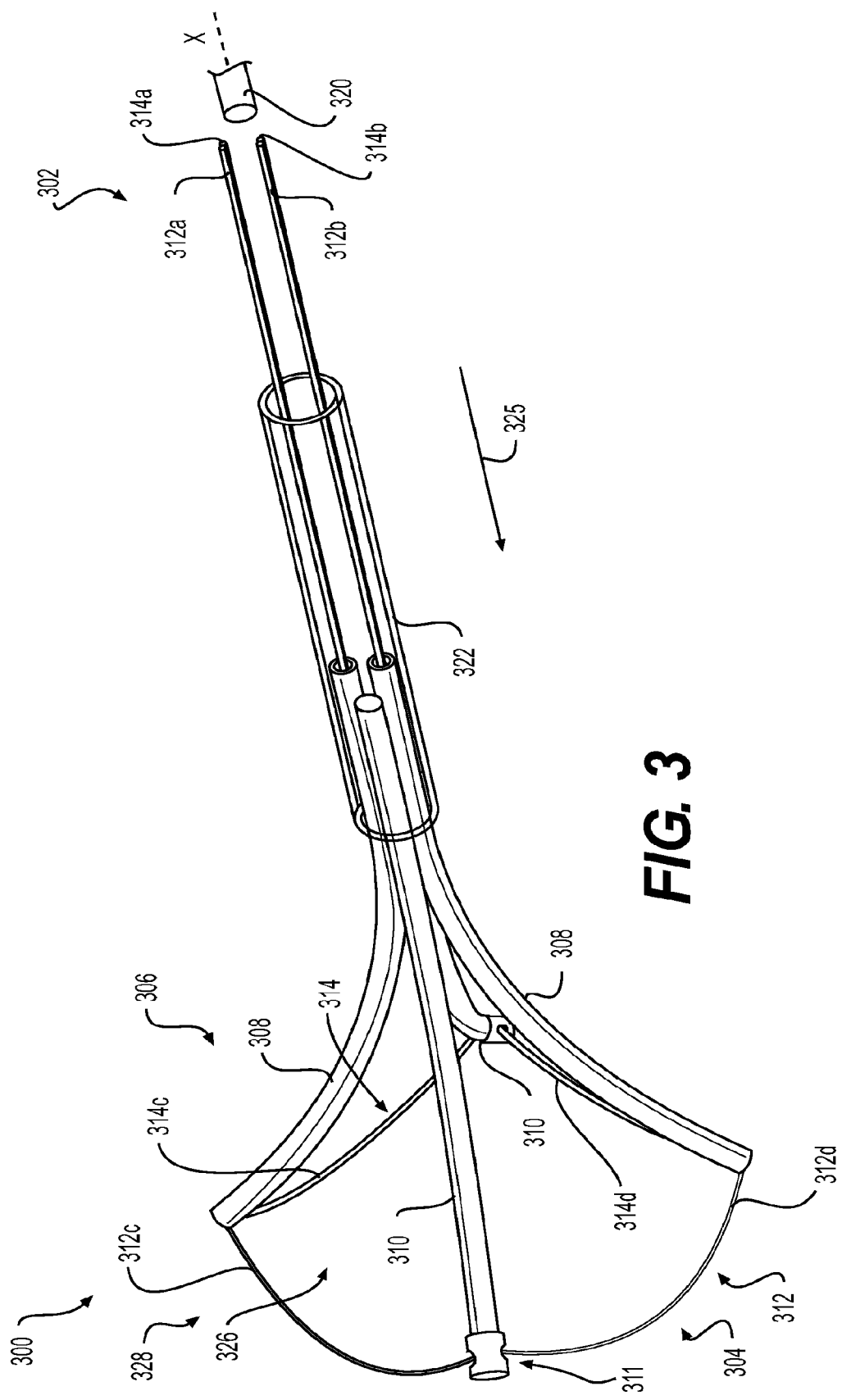
FIG. 3 is a partial side perspective view illustration of a medical retrieval device in an expanded configuration in accordance with an embodiment of the present disclosure.

As shown in FIG. 3, a medical device 300 according to an exemplary embodiment of the present disclosure may extend from a proximal end 302 toward a distal end 304. Medical device 300 may include a basket 306 disposed at distal end 304, and may be configured to reciprocally move between a collapsed configuration and an expanded configuration. In the embodiment shown in FIG. 3, basket 306 is in the expanded configuration. In the expanded configuration, a plurality of first branch members 308 and a plurality of second branch members 310 may be disposed radially outward about a longitudinal axis X of medical device 300. The plurality of first and second branch members 308, 310 may be circumferentially spaced apart from one another about longitudinal axis X. First branch members 308 may alternate with second branch members 310 such that each first branch member 308 may be circumferentially adjacent at least two second branch members 310. Similarly, each second branch member 310 may be circumferentially adjacent to at least two first branch members 308. In the embodiment shown in FIG. 1, two first branch members 308 and two second branch members 310 are disposed circumferentially about longitudinal axis X, and each first branch member 308 may be disposed about 90° from an adjacent second branch member 310. However, it should be noted that any other suitable number of first and second branch members 308, 310 may alternatively be utilized, if desired.

In some embodiments, first branch members 308 may be substantially similar to first branch members 108 described with reference to FIG. 1. Second branch members 310 may be generally tubular and have a cap with transverse bore 311 disposed at a distal end. In some embodiments, second branch members may be formed of a solid or hollow tube, though other suitable configurations are also contemplated. The cap may have any useful shape, including, e.g., a dome shaped cap to reduce potential for trauma in vivo. Transverse bore 311 may extend in a direction that is substantially perpendicular to a longitudinal axis of second branch member 310 and medical device 300. The exterior of second branch members 310 may be roughened, notched, slotted, etched, sand-blasted, or otherwise modified to provide a better gripping surface.

In the embodiment of FIG. 3, medical device 300 may include a first movable member 312 having a first end 312a, a second end 312b, and a midpoint that is fixed within a transverse bore 311 of one of the second branch members 310. Medical device 300 may also include a second movable member 314 having a first end 314a, a second end 314b, and a midpoint fixed within another transverse bore 311 of another of the second branch members 310. That is, the respective midpoints of first and second movable members 312, 314 may be fixed within different transverse bores 311 of respective second branch members 310 by any suitable mechanism, such as, e.g., adhesives, knotting, crimping member, or the like. First and second movable members 312, 314 may be substantially similar to first and second movable members 112, 114 described with reference to FIG. 1.

From its midpoint, first movable member 312 may include bridge portions 312c and 312d that extend distally from a respective transverse bore 311 toward separate first branch members 308. Similarly, second movable member 314 may include bridge portions 314c and 314d that extend distally from a respective transverse bore 311 toward separate first branch members 308. It should be noted that at least a portion of both first and second movable members 312, 314 may extend through each first branch member 308 toward proximal end 302. First and second movable members 312 and 314 may be coupled to an actuation member 320 via ends 312a, 312b, 314a, and 314b. Actuation member 320 may be substantially similar to actuation member 120 described with reference to FIG. 1.

A sheath 322 may be disposed around the proximal ends of first and second branch members 308, 310. In some embodiments, the proximal ends of first branch members 308 may be staggered from the proximal ends of second branch members 310 to facilitate attachment of first and second branch members 308, 310 within sheath 322. First and second branch members 308, 310 may be secured within sheath 322 in a substantially similar manner as first and second branch members 108, 110, and sheath 122 described with reference to FIG. 1.

First and second movable members 312, 314 may move along a path 325 that travels substantially along longitudinal axis X in order to reciprocally move basket 306 between the expanded and the collapsed configurations. Thus, first and second movable members 312, 314 may slide within first branch members 308. The proximal movement of first and second movable members 312, 314 may move basket 306 from the expanded configuration of FIG. 3 to the collapsed configuration of FIG. 4. The distal movement of first and second movable members 312, 314, may move basket 306 from the collapsed configuration to the expanded configuration.

In the expanded configuration, a user may manipulate medical device 300 to capture materials within a patient, such as, e.g., a kidney stone or the like. Materials may enter basket 306 via one of a plurality of side openings 326 defined by adjacent first and second branch members 308, 310, or via a distal opening 328 defined by bridge portions 312c, 312d, 314c, and 314d.

In some embodiments, first and second branch members 308, 310 may be biased (e.g., pre-bent or curved) such that in the expanded configuration of FIG. 3, the plurality of first and second branch members 308, 310 are naturally urged radially outward from longitudinal axis X. Alternatively, first and second branch members 308, 310 may be unbiased. Branch members 308, 310 include reinforcement, such as, e.g., a knitted filament braid with the wall of branch members 308, 310, wherein such reinforcement of the branch members further allows for deformation of the branch member in a pre-bent bias. The knitted filament may include metal, polymers, and combinations thereof.

Figure 4:
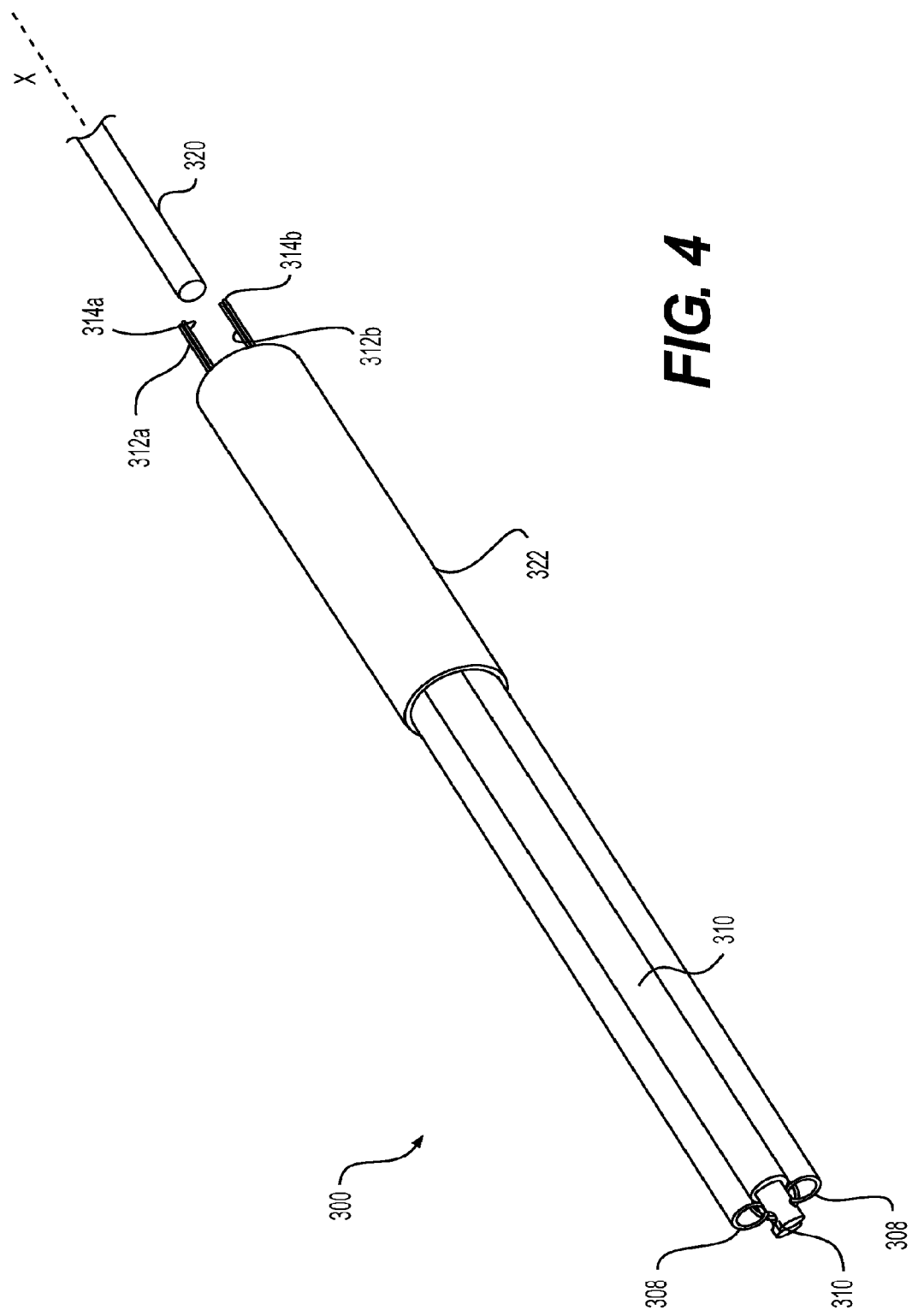
FIG. 4 is a partial side perspective view illustration of the medical retrieval device of FIG. 2 in a collapsed configuration.

In FIG. 4, medical device 300 is shown in the collapsed configuration. In the collapsed configuration, each first and second branch member 308, 310 may be substantially parallel to longitudinal axis X. That is, each first and second branch member 308, 310 may be directed radially inward toward longitudinal axis X from the expanded configuration as a result of the proximal retraction of actuation member 320 and/or first and second movable members 312, 314. In the collapsed configuration, bridge portions 312c, 312d, 314c, and 314d may be shorter than in the expanded configuration of medical device 300. Additionally, side openings 326 and distal opening 328 (referring to FIG. 3) may be closed in the collapsed configuration.

As shown in FIG. 5, a branch member 500 according to an exemplary embodiment of the present disclosure may extend from a proximal end 502 toward a distal end 504. Branch member 500 may alternatively be used in medical device 300 as a substitute for second branch members 310. Branch member 500 may be a wire formed from, e.g., stainless steel, nitinol or another suitable material. The exterior surface of branch member 500 may be roughened, notched, slotted, etched, sand-blasted, coated, or otherwise modified to provide a better gripping surface. Branch member 500 may be formed such that ends 500a and 500b are disposed at proximal end 502, and an eyelet 506 may be disposed at distal end 504 of branch member 500. Eyelet 506 may be a single loop, a coil, a knot, or another suitable eyelet mechanism. Lengths 507 of branch member 500 may be welded, glued, twisted, or jointed by any suitable mechanism, and may have the same or different lengths if desired. Proximal end 502 may be secured within, e.g., sheath 322 (referring to FIG. 3) by an adhesive, such as, e.g., glue or cyanoacrylate, or even by melting an additional piece of material such as that used in sheath 322. It should be noted, however, that any other suitable adhesive, or securing mechanism may alternatively be utilized. A movable member 510 may extend through eyelet 506, and the respective ends 510a and 510b of movable member 510 may be directed through a first branch member, e.g., first branch members 308 of FIG. 3. As best seen in FIG. 6, movable member 510 may include a lock section 512 that is disposed between and substantially perpendicular to lengths 514 and 515 of movable member 510. Lock section 512 may be formed by two approximately 90° bends (e.g., bends that are offset from the lengths of lengths 514 and 515) and may help positionally secure lock section 512 around eyelet 506 to ensure proper operation of a medical device utilizing movable member 510 during movement between the expanded and collapsed configurations of medical device 300. Additionally or alternatively, movable member 510 may be secured within eyelet 506 by crimping member, adhesive, or another suitable mechanism.

Figure 7:
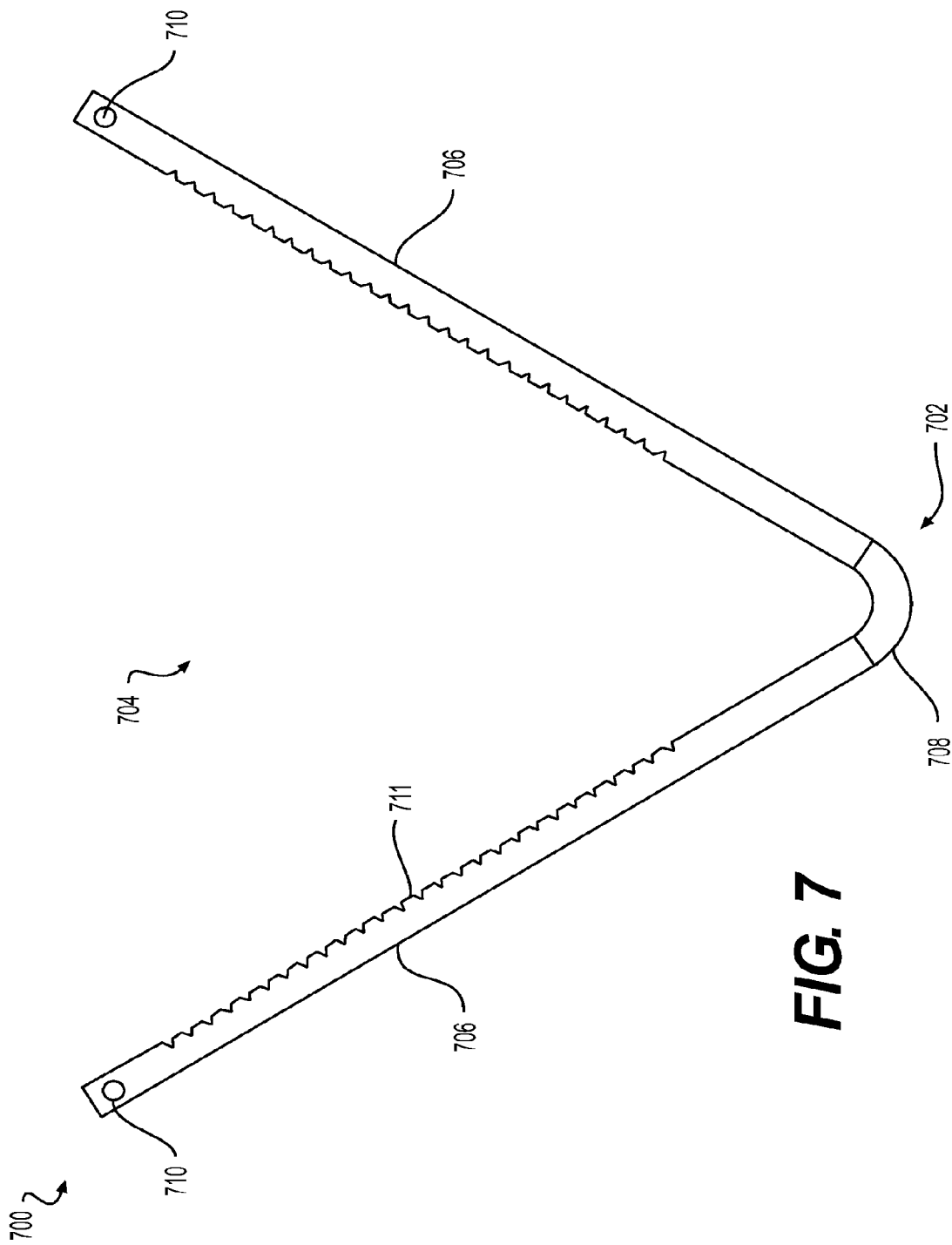
FIG. 7 is a front view illustration of a branch assembly in accordance with an embodiment of the present disclosure.

As shown in FIG. 7, a branch assembly 700 according to an exemplary embodiment of the present disclosure may extend from a proximal end 702 toward a distal end 704. Branch assembly 700 may include a pair of branch members 706 coupled to each other at a proximal bend 708 that generally form a v-shape. Branch assembly 700 may alternatively be used in medical device 300 as a substitute for a given pair of second branch members 310. Branch assembly 700 may be formed of a polymer, metal, other suitable material, or a combination thereof. Each branch member 706 may include a transverse bore 710, and each transverse bore 710 may hold a respective movable member in a manner similar to transverse bores 311 and eyelets 506 described with reference to FIGS. 3 and 5. A plurality of teeth 711 may be disposed on branch members 706 to provide a better gripping surface for materials, such as, e.g., kidney stones. Additionally, the exterior surface of branch members 706 may be roughened, notched, slotted, etched, sand-blasted, coated or otherwise modified to provide a better gripping surface. Proximal end 702 may be secured within sheath 322 (referring to FIG. 3) by an adhesive, such as, e.g., glue or cyanoacrylate, or even by melting an additional piece of material such as that used in sheath 322. It should be noted, however, that any other suitable adhesive, or securing mechanism may alternatively be utilized.

Figure 8:
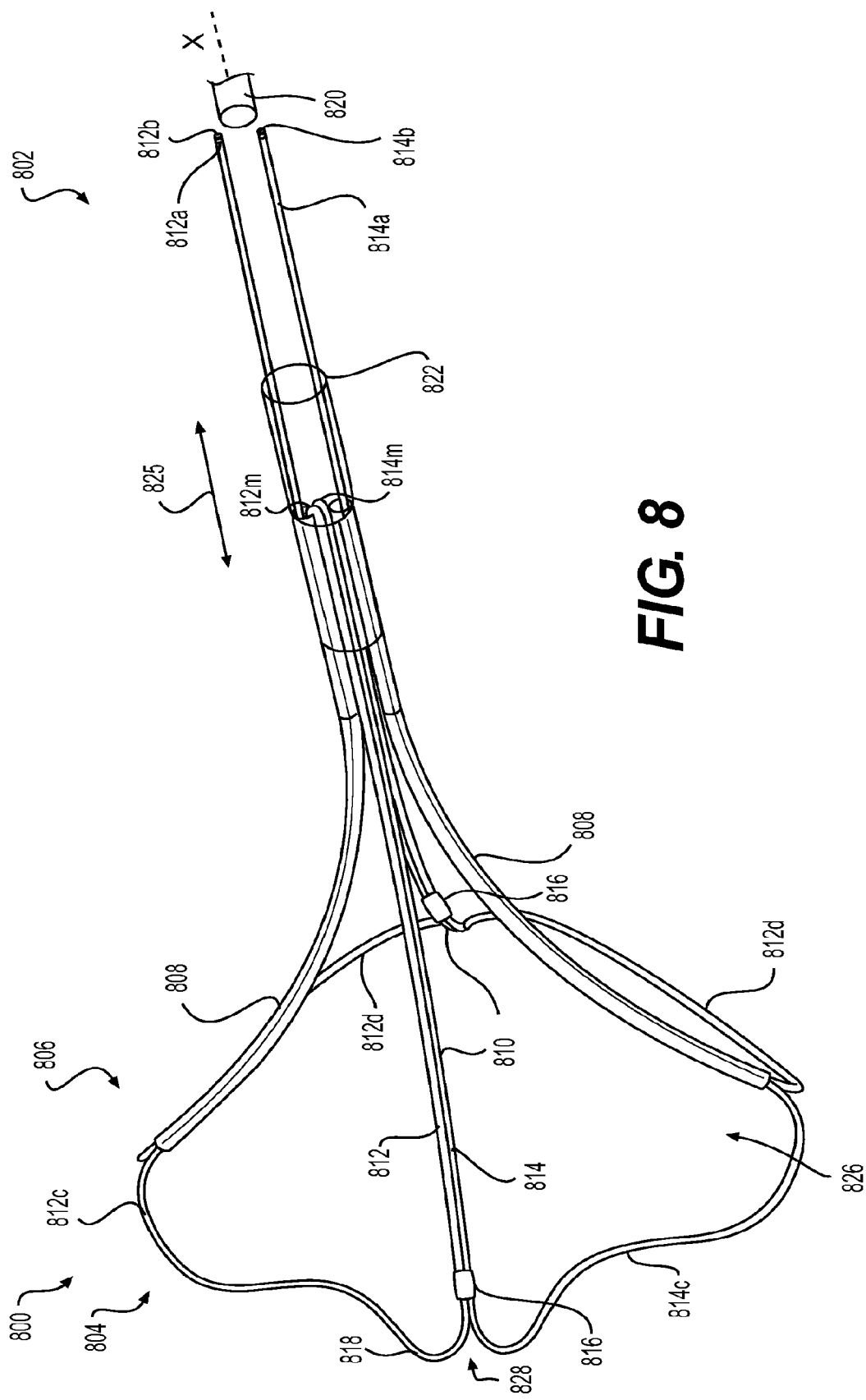
FIG. 8 is partial side perspective view illustration of a medical retrieval device in an expanded configuration in accordance with an embodiment of the present disclosure.

As shown in FIG. 8, a medical device 800 according to an exemplary embodiment of the present disclosure may extend from a proximal end 802 toward a distal end 804. Medical device 800 may include a basket 806 disposed at distal end 804, and may be configured to reciprocally move between a collapsed configuration and an expanded configuration. In the embodiment shown in FIG. 8, basket 806 is in the expanded configuration. In the expanded configuration, a plurality of first branch members 808 and a plurality of second branch members 810 may be disposed radially outward about a longitudinal axis X of medical device 800. The plurality of first and second branch members 808, 810 may be circumferentially spaced apart from one another about longitudinal axis X. First branch members 808 may alternate with second branch members 810 such that each first branch member 808 may be circumferentially adjacent at least two second branch members 810. Similarly, each second branch member 810 may be circumferentially adjacent to at least two first branch members 808. In the embodiment shown in FIG. 1, two first branch members 808 and two second branch members 810 are disposed circumferentially about longitudinal axis X, and each first branch member 808 may be disposed about 90° from an adjacent second branch member 810. However, it should be noted that any other suitable number of first and second branch members 808, 810 may alternatively be utilized, if desired.

In some embodiments, first branch members 808 may be substantially similar to first branch members 108 described with reference to FIG. 1. Second branch members 810 may be formed from joined sections of a first movable member 812 and a second movable member 814.

In the embodiment of FIG. 8, first movable member 812 may have a first end 812a, a second end 812b, and a midpoint 812m that is disposed within a sheath 822. Second movable member 814 may have a first end 814a, a second end 814b, and a midpoint 814m disposed within sheath 822. First and second movable members 812, 814 may be substantially similar to first and second movable members 112, 114 described with reference to FIG. 1.

From midpoint 812m, first movable member 112 may extend distally to form a portion of each of the plurality of second branch members 810. First movable member 812 may include bridge portions 812c and 812d that extend distally from the distal ends of separate second branch members 810 into a single first branch member 808. From midpoint 814m, second movable member 814 may extend distally to form another portion of each of the plurality of second branch members 810. Second movable member 814 may include bridge portions 814c and 814d that extend distally from the distal ends of separate second branch members 810 into a single first branch member 808. As shown in FIG. 8, bridge portions 812c and 812d may extend through a different first branch member 808 than bridge portions 814c and 814d extend through. It should be further noted that each second branch member 810 may be formed via a fixed portion of both first and second movable members 812 and 814. A crimping member 816 may be disposed at a distal end of each second branch member 816 to secure the respective fixed portions of first and second movable members 812 and 814 that form a second branch member 810 together. Crimping member 816 may be any suitable fastening mechanism such as, e.g., a crimped hypotube, weld, knot, wire twist, coil, heat shrink, or the like.

Ends 812a and 812b of first movable member 812 may extend through a respective first branch member 808 toward proximal end 802. Similarly, ends 814a and 814b of second movable member 814 may extend through a different respective first branch member 808 toward proximal end 802. First and second movable members 812 and 814 may be coupled to an actuation member 820 via ends 812a, 812b, 814a, and 814b. Actuation member 820 may be substantially similar to actuation member 120 described with reference to FIG. 1.

Sheath 822 may be disposed around the proximal ends of first and second branch members 808, 810. First and second branch members 808, 810 may be secured within sheath 822 in a substantially similar manner as first and second branch members 108, 110, and sheath 122 described with reference to FIG. 1.

First and second movable members 812, 814 may move along a path 825 that travels substantially along longitudinal axis X in order to reciprocally move basket 806 between the expanded and the collapsed configurations. Thus, first and second movable members 812, 814 may slide within first branch members 808. The proximal movement of first and second movable members 812, 814 may move basket 806 from the expanded configuration of FIG. 8 to the collapsed configuration of FIG. 9. The distal movement of first and second movable members 812, 814, may move basket 806 from the collapsed configuration to the expanded configuration.

In the expanded configuration, a user may manipulate medical device 800 to capture materials within a patient, such as, e.g., a kidney stone or the like. Materials may enter basket 806 via one of a plurality of side openings 826 defined by adjacent first and second branch members 808, 810, or via a distal opening 828 defined by bridge portions 812c, 812d, 814c, and 814d.

In some embodiments, first and second branch members 808, 810 may be biased (e.g., pre-bent or curved) such that in the expanded configuration of FIG. 8, the plurality of first and second branch members 808, 810 are naturally urged radially outward from longitudinal axis X. Further, in the embodiment of FIG. 8, first and second movable members 812, 814 may include one or more bends, such as, e.g., a bend 818 distal to each crimping member 816. Alternatively, first and second branch members 808, 810 may be unbiased. Branch members 808 include reinforcement, such as, e.g., a knitted filament braid with the wall of branch members 808, wherein such reinforcement of the branch members further allows for deformation of the branch member in a pre-bent bias. The knitted filament may include metal, polymers, and combinations thereof.

In FIG. 9, medical device 800 is shown in the collapsed configuration. In the collapsed configuration, each first and second branch member 808, 810 may be substantially parallel to longitudinal axis X. That is, each first and second branch member 808, 810 may be directed radially inward toward longitudinal axis X from the expanded configuration as a result of the proximal retraction of actuation member 820 and/or first and second movable members 812, 814. In the collapsed configuration, bridge portions 812c, 812d, 814c, and 814d may be shorter than in the expanded configuration of medical device 800. Additionally, side openings 826 and distal opening 828 (referring to FIG. 8) may be closed in the collapsed configuration.

In an alternative embodiment, bridge portions 812c, 812d, 814c, and 814d may each be formed from separate wires. That is, bridge portions 812c and 814c may be formed from separate wires joined by crimping member 816 at distal end 804, and secured within sheath 822 at a proximal end. Similarly, bridge portions 812d and 814d may be formed from separate wires joined by another crimping member 816 at distal end 804, and secured within sheath 822 at a proximal end.

An exemplary branch assembly 1000 is depicted in FIG. 10. Branch assembly 1000 may include a knot 1001 formed from a first movable member 1002 and a separate fixed member 1004. The first and second movable members 812, 814 (referring to FIG. 8) may, in some alternative embodiments, be substituted by two knot assemblies 1000. In this alternative configuration, fixed member 1004 may be fixed within sheath 822 at a proximal end, and may be movable between an expanded configuration and a collapsed configuration in a substantially similar manner to second branch member 810 (referring to FIG. 8). Respective lengths 1002a and 1002b of first movable member 1002 may extend through and be slidable within respective first branch members, such as, e.g., first branch members 808 (referring to FIG. 8).

All or a portion of the medical devices of the present disclosure may be formed of a radiopaque material so that they can be visualized under fluoroscopic guidance, or include an otherwise suitable imaging marker to indicate the position of the medical devices in vivo.

The disclosed medical devices may be utilized in any suitable application requiring the capture and removal of materials from the body. The disclosed medical devices may be simple and inexpensive to manufacture, and have improved durability as they may have fewer components prone to failure.

Any aspect set forth in any embodiment may be used with any other embodiment set forth herein. The devices and apparatus set forth herein may be used in any suitable medical procedure, may be advanced through any suitable body lumen and body cavity, and may be used to remove material from any suitable body portion. For example, the apparatuses and methods described herein may be used through any natural body lumen or tract, including those accessed orally, vaginally, rectally, nasally, urethrally, or through incisions in any suitable tissue.

The disclosed medical devices may be configured to capture fragments having dimensions of about 3 French or smaller. In some embodiments, the disclosed medical devices may be able to capture and release smaller stones having diameters from 1 mm to 12 mm. In some embodiments, a user may want to reposition larger stones from the lower calyx to the upper calyx of the kidney to be broken with a laser before removing them through a small diameter of the ureter. The stones may be removed in front of a scope, as opposed to through scope channel to prevent damage to a scope channel. When stones are removed, both an endoscope and a medical device may be removed from the human body. In some embodiments, a guide sheath for a ureteroscope may be used to guide the ureteroscope and medical device back to a previous position or to a new position to capture additional stones, and protect a ureter wall during stone removal. While moving from the expanded configuration to the collapsed configuration, medical devices of the present disclosure may ligate larger stones and capture smaller stones within a basket.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only. The following disclosure identifies some other exemplary embodiments.

I claim:

1. A medical device, comprising:
    a plurality of first branch members;
    a plurality of second branch members;
    a first movable member; and
    a second movable member, wherein, the plurality of first and second branch members and the first and second movable members form a basket movable between a collapsed configuration and an expanded configuration, wherein each of the plurality of second branch members includes an eyelet disposed at a distal end of the second branch member, wherein the first movable member extends through an eyelet of one of the plurality of second branch members, the second movable member extends through an eyelet of another of the plurality of second branch members; and
    wherein the first and second movable members each include:
        a first end;

a second end; and a lock section disposed between the first and second ends, the lock section being between each of the first and second ends by a bend that is offset from the lengths of the first and second ends; and wherein the lock section is secured to the eyelet.

2. The medical device of claim 1, wherein the first and second branch members alternate circumferentially about a longitudinal axis of the medical device.

3. The medical device of claim 1, wherein each of the plurality of first branch members includes a tube having a portion of at least one of the first and second movable members disposed therethrough.

4. The medical device of claim 1, wherein each of the plurality of second branch members includes a tube having a portion of each of the first and second movable members disposed therethrough.

5. The medical device of claim 1, further including a sheath coupled to a proximal end of each of the plurality of first and second branch members, wherein at least one end of each of the plurality of first and second movable members extend proximally within the sheath.

6. The medical device of claim 1, wherein the plurality of second branch members, the first movable member, and the second movable member are joined in a branch assembly.

7. The medical device of claim 1, wherein two portions of the first movable member extend distally from different second branch members of the plurality of second branch members and back through a same first branch member of the plurality of first branch members.

8. The medical device of claim 7, wherein two ends of the second movable member extends distally from different second branch members of the plurality of second branch members and back through a same first branch member of the plurality of first branch members.

9. The medical device of claim 8, wherein the respective two ends of each of the first and second movable members extend through different first branch members of the plurality of first branch members.

* * * * *